(12) United States Patent
Davis et al.

(10) Patent No.: US 10,342,613 B2
(45) Date of Patent: *Jul. 9, 2019

(54) SYSTEMS AND METHODS FOR REDUCTION OF ATRIAL FIBRILLATION

(71) Applicant: Coherex Medical, Inc., Salt Lake City, UT (US)

(72) Inventors: Clark C. Davis, Holladay, UT (US); Richard J. Linder, Sandy, UT (US); Scott D. Miles, Sandy, UT (US); Daryl R. Edmiston, Draper, UT (US)

(73) Assignee: Coherex Medical, Inc., Salk Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,556

(22) Filed: Jan. 3, 2018

(65) Prior Publication Data

US 2018/0125578 A1 May 10, 2018

Related U.S. Application Data

(60) Continuation of application No. 15/365,873, filed on Nov. 30, 2016, now Pat. No. 9,867,662, which is a
(Continued)

(51) Int. Cl.
*A61B 18/14* (2006.01)
*A61B 18/08* (2006.01)
(Continued)

(52) U.S. Cl.
CPC ........ *A61B 18/1492* (2013.01); *A61B 18/082* (2013.01); *A61B 18/18* (2013.01);
(Continued)

(58) Field of Classification Search
CPC .......... A61B 5/042; A61B 2017/00367; A61B 2017/0046; A61B 2017/00575;
(Continued)

(56) References Cited

U.S. PATENT DOCUMENTS 3,814,104 A  6/1974 Imich et al.
5,078,714 A  1/1992 Katims
(Continued)

FOREIGN PATENT DOCUMENTS

EP  1518518 A2  3/2005

OTHER PUBLICATIONS

International Search Report dated Aug. 12, 2009 for International Application No. PCT/US2009/031903 (3 Pages).

*Primary Examiner* — Manuel A Mendez
(74) *Attorney, Agent, or Firm* — David L. Stott

(57) ABSTRACT

Embodiments of the present invention are directed to ablation catheter systems configured, for example, to ablate tissue adjacent an ostium of the pulmonary vein in a left atria of a heart. In one embodiment, an ablation catheter system includes a handle and a catheter coupled to the handle defining a lumen extending through a length of the catheter, the catheter including a distal end thereof. The ablation catheter system may also include an electrode coupled to the handle with lines extending through the lumen of the catheter, the electrode being configured to be constrained adjacent the distal end of the catheter and configured to be deployed from the distal end of the catheter to an expanded configuration.

20 Claims, 12 Drawing Sheets

Related U.S. Application Data continuation of application No. 14/715,338, filed on May 18, 2015, now Pat. No. 9,510,892, which is a continuation of application No. 14/143,913, filed on Dec. 30, 2013, now Pat. No. 9,044,233, which is a continuation of application No. 13/567,597, filed on Aug. 6, 2012, now Pat. No. 8,636,732, which is a division of application No. 12/359,223, filed on Jan. 23, 2009, now Pat. No. 8,235,988.

(60) Provisional application No. 61/114,863, filed on Nov. 14, 2008, provisional application No. 61/023,378, filed on Jan. 24, 2008.

(51) Int. Cl.
*A61B 18/18* (2006.01)
*A61B 18/00* (2006.01)
*A61B 17/00* (2006.01)
*A61B 5/042* (2006.01)
*A61M 25/01* (2006.01)
*A61M 25/10* (2013.01)

(52) U.S. Cl.
CPC ....... *A61B 5/042* (2013.01); *A61B 2017/0046* (2013.01); *A61B 2017/00367* (2013.01); *A61B 2017/00575* (2013.01); *A61B 2017/00867* (2013.01); *A61B 2018/0022* (2013.01); *A61B 2018/00214* (2013.01); *A61B 2018/00267* (2013.01); *A61B 2018/00351* (2013.01); *A61B 2018/00375* (2013.01); *A61B 2018/00577* (2013.01); *A61B 2018/00839* (2013.01); *A61B 2018/1435* (2013.01); *A61M 2025/0183* (2013.01); *A61M 2025/1047* (2013.01); *A61M 2025/1052* (2013.01)

(58) Field of Classification Search
CPC ........... A61B 2017/00867; A61B 2018/00214; A61B 2018/0022; A61B 2018/00267; A61B 2018/00351; A61B 2018/00375; A61B 2018/00577; A61B 2018/00839; A61B 2018/1435; A61M 2025/0183; A61M 2025/1047; A61M 2025/1052

USPC ............... 604/22; 606/41, 49; 607/113, 112; 600/372, 374, 381
See application file for complete search history.

(56) References Cited

U.S. PATENT DOCUMENTS

| | | |
|---|---|---|
| 5,308,325 A | 5/1994 | Quinn et al. |
| 5,311,866 A | 5/1994 | Kagan et al. |
| 5,327,889 A | 7/1994 | Imran |
| 5,331,779 A | 7/1994 | Hing |
| 5,397,341 A | 3/1995 | Hirschberg et al. |
| 5,465,717 A | 11/1995 | Imran et al. |
| 5,500,012 A | 3/1996 | Brucker et al. |
| 5,800,350 A | 9/1998 | Coppleson et al. |
| 5,972,026 A | 10/1999 | Laufer et al. |
| 6,024,740 A | 2/2000 | Lesh et al. |
| 6,071,282 A | 6/2000 | Fleischman |
| 6,117,101 A | 9/2000 | Diederich et al. |
| 6,164,283 A | 12/2000 | Lesh |
| 6,165,169 A | 12/2000 | Panescu et al. |
| 6,216,043 B1 | 4/2001 | Swanson et al. |
| 6,245,064 B1 | 6/2001 | Lesh et al. |
| 6,254,599 B1 | 7/2001 | Lesh et al. |
| 6,383,151 B1 | 5/2002 | Diederrich et al. |
| 6,416,511 B1 | 7/2002 | Lesh et al. |
| 6,572,612 B2 | 6/2003 | Stewart et al. |
| 6,632,223 B1 | 10/2003 | Keane |
| 6,669,693 B2 | 12/2003 | Friedman |
| 6,672,312 B2 | 1/2004 | Acker |
| 6,702,811 B2 | 3/2004 | Stewart et al. |
| 6,752,805 B2 | 6/2004 | Maguire et al. |
| 6,837,886 B2 | 1/2005 | Collins et al. |
| 6,872,205 B2 | 3/2005 | Lesh et al. |
| 6,893,438 B2 | 5/2005 | Hall et al. |
| 6,960,206 B2 | 11/2005 | Keane |
| 7,052,493 B2 | 5/2006 | Vaska et al. |
| 7,195,628 B2 | 3/2007 | Falkenberg |
| 7,306,594 B2 | 12/2007 | Collins et al. |
| 7,413,568 B2 | 8/2008 | Swanson et al. |
| 8,235,988 B2 | 8/2012 | Davis et al. |
| 8,636,732 B2 | 1/2014 | Davis et al. |
| 9,044,233 B2 | 6/2015 | Davis et al. |
| 9,867,662 B2 * | 1/2018 | Davis ................... A61B 18/082 |
| 2002/0143349 A1 | 10/2002 | Gifford, III et al. |
| 2003/0074039 A1 | 4/2003 | Puskas |
| 2003/0181901 A1 | 9/2003 | Maguire et al. |
| 2005/0222563 A1 | 10/2005 | McDaniel et al. |

* cited by examiner

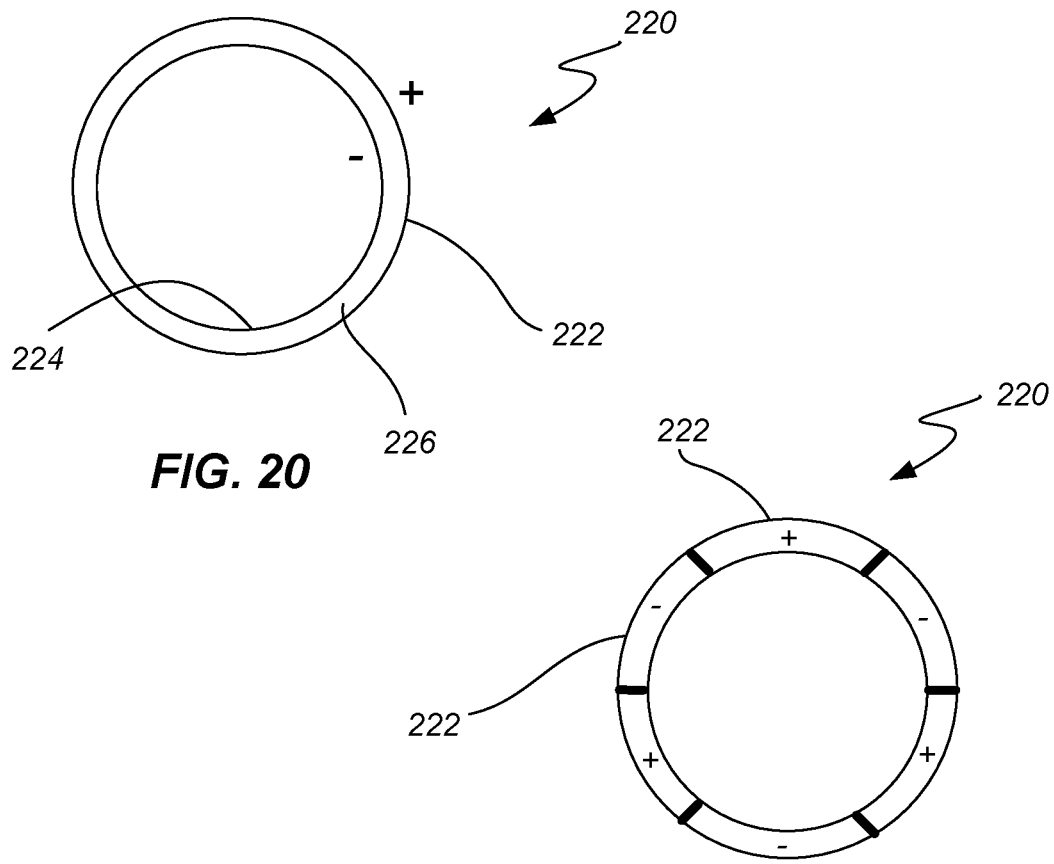
FIG. 20
FIG. 21
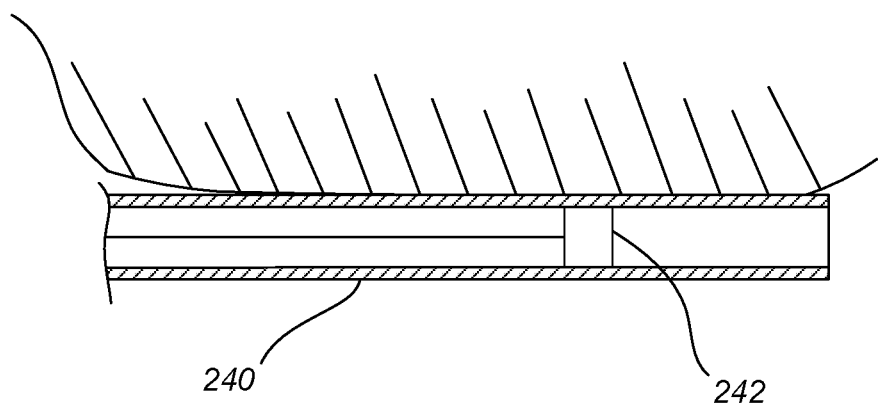
FIG. 22

SYSTEMS AND METHODS FOR REDUCTION OF ATRIAL FIBRILLATION

CROSS-REFERENCE TO RELATED APPLICATIONS

The present application is a continuation of U.S. Non-Provisional patent application Ser. No. 15/365,873, filed Nov. 30, 2016, now U.S. Pat. No. 9,867,662, which is a continuation of U.S. Non-Provisional application Ser. No. 14/715,338, filed May 18, 2015, now U.S. Pat. No. 9,510,892, which is a continuation of U.S. Non-Provisional application Ser. No. 14/143,913, filed Dec. 30, 2013, now U.S. Pat. No. 9,044,233, which is a continuation of U.S. Non-Provisional application Ser. No. 13/567,597, filed Aug. 6, 2012, now U.S. Pat. No. 8,636,732, which is a divisional of U.S. Non-Provisional application Ser. No. 12/359,223, filed Jan. 23, 2009, now U.S. Pat. No. 8,235,988, which claims the benefit and priority of Provisional Application Ser. No. 61/023,378, filed Jan. 24, 2008, and Provisional Application Ser. No. 61/114,863, filed Nov. 14, 2008, the disclosures of each of which are incorporated herein in their entireties by reference.

TECHNICAL FIELD

The present invention relates generally to ablation systems and methods and, more specifically, to systems and methods for reduction of atrial fibrillation including various electrode configurations and ablation catheter systems.

BACKGROUND

The heart includes a number of pathways that are responsible for the propagation of signals necessary to produce continuous, synchronized contractions. Each contraction cycle begins in the right atrium where a sinoatral node initiates an electrical impulse. This impulse then spreads across the right atrium to the left atrium, stimulating the atria causing them to contract. The chain reaction continues from the atria to the ventricles by passing through a pathway known as the atrioventricular (AV) node or junction, which acts as an electrical gateway to the ventricles. The AV junction delivers the signal to the ventricles while also slowing or delaying it, so the atria can relax before the ventricles contract.

Disturbances in the heart's electrical system may lead to various rhythmic problems that can cause the heart to beat irregularly, too fast or too slow. Irregular heart beats, or arrhythmia, are caused by physiological or pathological disturbances in the discharge of electrical impulses from the sinoatrial node, in the transmission of the signal through the heart tissue, or by spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possibly other locations). These unexpected electrical impulses produce irregular, often rapid heartbeats in the atrial muscles and ventricles. Patients experiencing atrial fibrillation may suffer from fatigue, activity intolerance, dizziness and even strokes.

The precise cause of atrial fibrillation, and in particular the depolarizing tissue causing "extra" electrical signals, is currently unknown. As to the location of the depolarizing tissue, it is generally agreed that the undesired electrical impulses often originate in the left atrial region of the heart. Recent studies have expanded upon this general understanding, suggesting that nearly 90% of these "focal triggers" or electrical impulses are generated in one (or more) of the four pulmonary veins (PV) extending from the left atrium. In this regard, as the heart develops from an embryotic stage, left atrium tissue may grow or extend a short distance into one or more of the PVs. It has been postulated that this tissue may spontaneously depolarize, resulting in an unexpected electrical impulse(s) propagating into the left atrium and along the various electrical pathways of the heart.

A variety of different atrial fibrillation treatment techniques are available, including drugs, surgery, implants, and catheter ablation. While drugs may be the treatment of choice for some patients, drugs typically only mask the symptoms and do not cure the underlying cause. Implantable devices, on the other hand, usually correct an arrhythmia only after it occurs, but do not cure the condition or prevent arrhythmias from occurring again in the future. Surgical and catheter-based treatments, in contrast, will actually cure the problem by ablating the abnormal tissue or accessory pathway responsible for the atrial fibrillation. The catheter-based treatments rely on the application of various destructive energy sources to the target tissue, including direct current electrical energy, radiofrequency (R) electrical energy, laser energy, and the like. The energy source, such as an ablating electrode, is conventionally disposed along a distal portion of a catheter.

Most ablation catheter techniques employed to treat atrial fibrillation focus upon locating the ablating electrode, or a series of ablating electrodes, along extended target sections of the left atrium wall. Because the atrium wall, and thus the targeted site(s), is relatively tortuous, the resulting catheter design includes multiple curves, bends, extensions, etc. In response to recent studies indicating that the unexpected electrical impulses are generated within a PV, efforts have been made to ablate tissue within the PV itself. Obviously, the prior catheter designs incorporating convoluted, multiple bends are not conducive to placement within a PV. Instead, a conventional "straight ended" ablation catheter has been employed. While this technique of tissue ablation directly within a PV has been performed with some success, such a technique is tedious and in not time efficient. As such, an improved ablation catheter that is more conducive to the anatomy and is more time efficient than the conventional "straight ended" ablation catheter would be desirable.

A related concern entails understanding the electrical characteristics of the tissue surrounding the PV prior to ablation. For example, for atrial fibrillation, it is necessary to identify the origination point of the undesired electrical impulses prior to ablation. Typically, an entirely separate catheter is employed for understanding the characteristics of the tissue prior to beginning an ablation process with an ablation catheter. These additional steps greatly increase the overall time required to complete the procedure.

Based on the foregoing, it is desirable to provide an ablation catheter that better conforms to the anatomy and overcomes the deficiencies of the conventional "straight ended" ablation catheter. Further, it may be desirable to provide an ablation catheter that does not require the additional acts that greatly increase the overall time required to understand the electrical characteristics of the tissue surrounding the PV.

BRIEF SUMMARY OF THE INVENTION

The present invention is directed to an ablation catheter system configured, for example, to ablate tissue adjacent an ostium of the pulmonary vein in a left atria of a heart. In one embodiment, the ablation catheter system includes a handle including an actuator and a catheter coupled to the handle defining a lumen extending through a length of the catheter, the catheter including a tip portion at a distal end thereof. The ablation catheter system also includes an electrode coupled to the handle with lines extending through the lumen of the catheter, the electrode being configured to be constrained within the tip portion of the catheter and configured to be deployed from the tip portion and self expand to an expanded configuration. In one embodiment, the electrode is configured to self expand to a substantially conical configuration with a tip portion configured to be disposed within the pulmonary vein.

In another embodiment, the ablation catheter system includes an energy source coupled to the electrode. The electrode includes one or more sensors coupled to a sensor display. The energy source may include or be coupled to a return electrode.

In another embodiment, the electrode includes a multicellular structure that is configured to expand radially outward. The electrode includes a tip portion configured to self center the electrode within a pulmonary vein with a proximal portion of the electrode configured to abut against tissue adjacent the ostium of the pulmonary vein.

In another embodiment, the tip portion includes a first lumen and a second lumen, wherein the first lumen coincides with the lumen of the catheter and the second lumen is positioned adjacent the first lumen and is configured to engage a guide wire in facilitating access to the left atrium of the heart. In still another embodiment, the ablation catheter system includes a push rod coupled to the electrode and is configured to stabilize the electrode.

In another embodiment, the present invention is directed to an electrode coupled to an ablation catheter system configured to ablate tissue adjacent an ostium of a pulmonary vein in a left atrium of a heart. The electrode includes a frame including multiple struts defining center portion cells, intermediate cells and outer cells. The intermediate cells being disposed between the center portion cells and the outer cells, and further, the intermediate cells extending radially outward from the center portion cells and the outer cells extending radially outward from the intermediate cells. With this arrangement, the frame is configured to move between a constricted narrow configuration and a radially self expanding configuration. Further, in one embodiment, the frame is configured to self expand to a conical configuration.

In another embodiment, the electrode includes center portion cells having common struts with the intermediate cells. In still another embodiment, the intermediate cells include common struts with the center portion cells and the outer cells.

In still another embodiment of the electrode, the outer cells include attachment structures, such as eyelets, configured to attach lines extending to the ablation catheter system.

In another embodiment, the frame is configured to self expand with a flange portion. Such a flange portion can be defined from at least one of the outer cells and the intermediate cells of the frame. The center portion cells can include a tip portion of the self expanded configuration of the electrode. Further, the tip portion is configured to self center the frame over the ostium of the pulmonary vein.

In another embodiment, the frame includes one or more sensors configured to sense characteristics of tissue adjacent the ostium of the pulmonary vein. In still another embodiment, the frame comprises a super elastic material.

In yet another embodiment, a catheter system for heating tissue adjacent an ostium of a pulmonary vein is provided. The system includes a catheter having a proximal portion and a distal portion. An RF energy source is operatively connected with the catheter and an electrode coupled to the RF source. The electrode is positioned adjacent the distal portion of the catheter and configured to heat at least one segment adjacent the ostium of the pulmonary vein.

In accordance with another embodiment, a method of ablating tissue adjacent an ostium of a pulmonary vein is provided. The method includes disposing an electrode adjacent a pulmonary vein and placing a centering device at least partially within the pulmonary vein. The electrode is positioned against tissue at or near the ostium of the pulmonary vein subsequent placing the centering device and Energy is provided to the electrode to ablate the tissue contacted by the electrode.

In accordance with another embodiment, a method of ablating tissue adjacent an ostium of a pulmonary vein is provided. The method includes disposing an electrode adjacent a pulmonary vein. Tissue is contacted with the electrode electrical characteristics of the tissue are measured through the electrode. The electrode is positioned in response to the measured electrical characteristics and tissue is ablated with the electrode.

BRIEF DESCRIPTION OF THE SEVERAL VIEWS OF THE DRAWINGS

The foregoing and other advantages of the invention will become apparent upon reading the following detailed description and upon reference to the drawings in which:

FIGS. 19A-9C show an electrode and catheter system according to another embodiment of the present invention;

FIGS. 20 and 21 show electrodes according to additional embodiments of the present invention; and FIG. 22 shows a catheter system in accordance with another embodiment of the present invention.

DETAILED DESCRIPTION OF THE INVENTION

Figure 1:
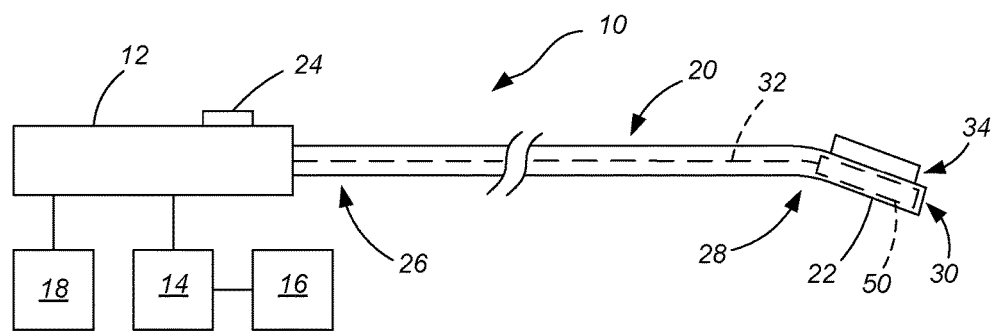
FIG. 1 shows a catheter system configured to enter the left atrium of the heart to ablate tissue adjacent the pulmonary vein, according to an embodiment of the present invention.

Referring first to FIG. 1, a catheter system 10 is shown which is configured to enter a left atrium of the heart (not shown) according to an embodiment of the invention. Such a catheter system 10 includes an electrode 50 that is sized and configured to ablate tissue at the ostium of the pulmonary vein within the left atrium of the heart. The catheter system 10 includes a handle 12, a catheter 20 and the electrode 50 disposed within a tip portion 22 of the catheter 20. The catheter system 10 may also include an energy source 14, a return electrode 16 and a sensor display 18 configured to display information being received from one or more sensors within or near the electrode 50. The catheter system 10 of the presently considered embodiment is configured to be employed as an ablation catheter under a uni-polar system, utilizing the return electrode 16. However, as will be recognized by one of ordinary skill in the art, the ablation catheter of the present invention can be utilized as a bi-polar system with minor modification.

Use of RF energy and associated electrodes is discussed in substantial detail in Applicants previously filed U.S. patent application Ser. No. 11/754,978, filed May 29, 2007, entitled METHODS, SYSTEMS, AND DEVICES FOR SENSING, MEASURING, AND CONTROLLING CLOSURE OF A PATENT FORAMEN OVALE, the disclosure of which is hereby incorporated by reference in its entirety, as well as Applicants previously filed U.S. patent application Ser. No. 11/754,963, filed May 29, 2007, entitled METHODS, SYSTEMS, AND DEVICES FOR CLOSING A PATENT FORAMEN OVALE USING MECHANICAL STRUCTURES, the disclosure of which is hereby incorporated by reference in its entirety.

The handle 12 may include an actuator 24 configured to deploy the electrode 50 from the catheter 20 as well as recapture or re-sheath the electrode 50 within the catheter 20. The catheter 20 includes a proximal portion 26 and a distal portion 28 with a lumen 30 extending through the length of the catheter 20. At the proximal portion 26 of the catheter 20, the catheter 20 is incorporated with the handle 12. The distal portion 28 of the catheter 20 includes the tip portion 22. The tip portion 22 may include a lumen that extends from, and coincides and is in communication with, the lumen 30 of the catheter 20. Such tip portion 22 is configured to house or hold the electrode 50 in a constricted and contained configuration. The electrode 50 is interconnected to the handle 12 via lines 32 (or tethers) and a push rod (see FIGS. 3 and 4) that can extend through a portion of, or fully through, the length of the lumen 30 of the catheter 20. The tip portion 22 may also include a rapid exchange (Rx) lumen 34 to facilitate accessing the left atrium of the heart via a guide wire (not shown). Such an Rx lumen 34, disposed in a non-coaxial arrangement with the lumen 30 of the catheter 20 or tip portion 22, is fully disclosed in Applicant's previously filed patent application, U.S. patent application Ser. No. 11/836,051, filed Aug. 8, 2007, the disclosure of which is hereby incorporated by reference in its entirety. It is also noted that the currently described catheter system 10 may also be adapted to facilitate over the wire access to the left atrium of the heart.

Figure 2:
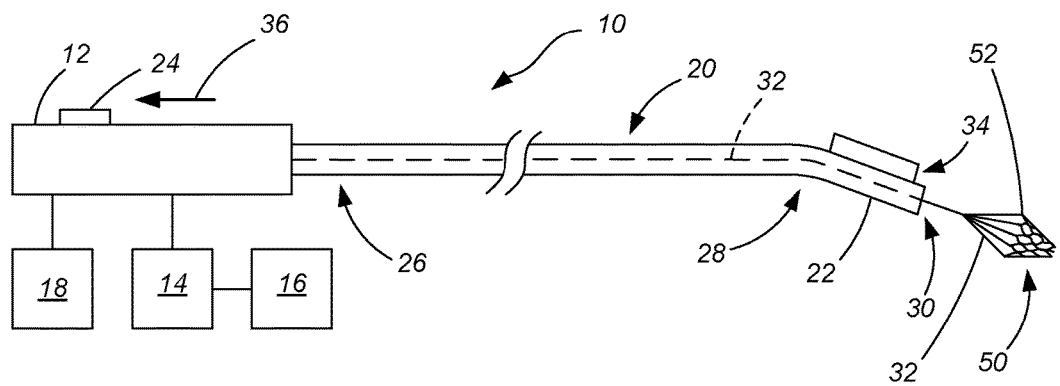
FIG. 2 shows the catheter system in FIG. 1 with a self expanding electrode deployed from the catheter system, according to an embodiment of the present invention.

Referring now to FIGS. 1 and 2, the catheter system 10 may be seen with the electrode 50 in a non-deployed position (FIG. 1) and a deployed position (FIG. 2). To deploy the electrode, the actuator 24 on the handle 12 can be manually moved as shown by arrow 36 from the position shown in FIG. 1 to the position shown in FIG. 2. A push-rod (not shown in FIGS. 1 and 2) may be associated with the actuator 24 to displace the electrode 50 in relationship to the tip 22 of the catheter 20. In another embodiment, the actuator 24 may be configured to move the catheter 20 proximally (relative to a push-rod or other structure) to facilitate un-sheathing the electrode 50 from the tip portion 22 of the catheter 20.

As depicted, the electrode 50 can be configured to automatically self expand to an enlarged, un-constricted and expanded configuration. Such expanded configuration of the electrode 50 may include a conical configuration or the like or any other shaped configuration, such as partially conical with a proximal outward extending flange, that will maximize the preferred area for ablating tissue at the ostium of the pulmonary vein. Further detail regarding the structure of the electrode 50 will be discussed below. In addition, at a proximal side of the electrode 50 there may be attachment points 52 for the lines 32 or tethers to couple thereto. The electrode 50 may be configured to move between a deployed configuration and the constrained non-deployed configuration within the tip portion 22. In addition to moving the catheter 20 to deploy the electrode 50 as described above, the actuator 24 may be utilized to displace the catheter 20 and recapture or resheath the electrode 50. In another embodiment, the electrode may be configured to be substantially flat when in a substantially unconstrained state. In such a case, the electrode may be configured to contact a greater area of tissue surrounding the ostium of a pulmonary vein.

The catheter 20 can access the left atrium of the heart via a guide wire (not shown). As such, the guide wire can be pushed through the femoral vein to access the left atrium via a trans-septal puncture using, for example, known techniques in the art. Once the guide wire has accessed the left atrium, the distal portion 28 of the catheter 20 can then access the left atrium by inserting the proximal end of the guide wire through the Rx lumen 34 of the tip portion 22. The catheter 20 is then moved distally through the vein to access the left atrium and the electrode 50 may be deployed from the tip portion 22 of the catheter 20. The electrode 50 may be positioned over the ostium of the pulmonary veins with a distal end of the electrode 50 extending within the pulmonary vein. In this position, the electrode 50 can be used to measure electrical signals of the muscle tissue with sensors on the electrode 50 (or with the electrode itself). Such sensors can determine characteristics of the tissue. This sensing of the tissue can facilitate the determination of which portion(s) of the tissue adjacent the pulmonary vein need to be treated and the proper position of the electrode 50 for such treatment.

In one embodiment, the electrode 50 itself may be used as a sensor, with one or more additional electrodes (e.g., a return electrode 16) acting in concert with the electrode 50 positioned at or near the pulmonary vein. In another embodiment, specific components or areas of the electrode 50 may be electrically isolated from one another such that the "electrode 50" itself acts as multiple electrodes. The electrode 50 may be used, for example, as an EKG electrode during one stage of the process while being used as a heating or ablating electrode during another stage of the process.

The one or more sensors (or electrodes) may be coupled to a controller for evaluating the electrical signals generated by such sensors. The sensors may also be coupled to a display 18 to provide feed back to the physician, based on the signals generated by the sensors, so the physician may understand and evaluate the characteristics of the tissue. This further helps the physician in understanding what the proper position and orientation of the electrode 50 should be, as well as the amount of energy or heat that should be applied to the tissue, in order to obtain the desired results from the ablative process. Once the physician is able to evaluate the characteristics of the tissue, the physician can then place the electrode 50 over the ostium and heat the tissue with RF energy (or other energy) via the energy source 14 in a manner consistent with that which was determined in the exploratory or investigative process.

In one embodiment, the electrode 50 may include a multi-cellular structure and exhibit generally conical or other tapered configuration. Such an electrode 50 is configured to maximize the tissue area at the ostium that is heated with the energy from the energy source 14. Further, according to the present invention, the generally conical configuration of the electrode 50 provides an inherent self centering feature by positioning a distal tip of the conical structure within the pulmonary vein and moving the electrode 50 forward so that the electrode 50 is positioned against the tissue adjacent the ostium of the pulmonary vein. After heating the tissue, the electrode 50 can again be utilized for sensing the characteristics of the tissue in order to determine if the tissue has been sufficiently treated as desired. This process can then be repeated in treating the tissue at the ostium for each of the four pulmonary veins as determined from the electrode 50. Once complete, the electrode 50 can be recaptured within the tip portion 22 of the catheter and withdrawn from the patient.

Figure 3:
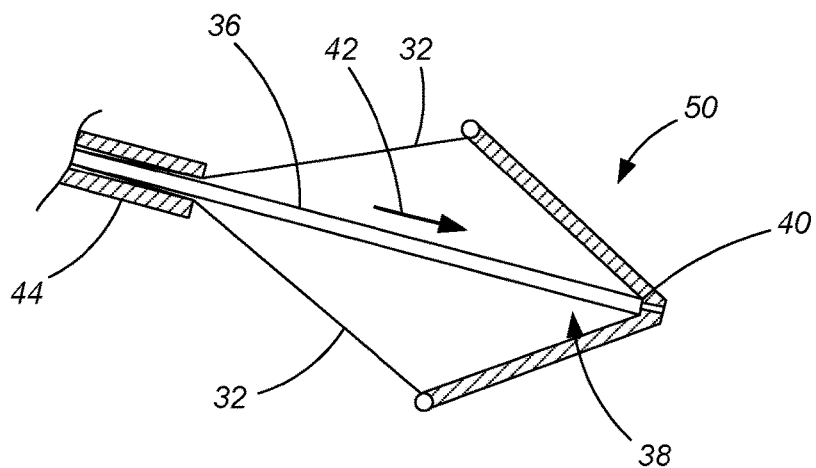
FIG. 3 is a partial cross-sectional view depicting another embodiment of the self expanding electrode with a pusher rod integrated with the catheter system, according to another embodiment of the present invention.

Referring to FIG. 3, a cross-sectional view of an electrode 50 is shown wherein a push rod 36 is utilized to assist in the placement and recapture of the electrode 50 during an ablation procedure. The electrode 50 is coupled with a push rod 36 which may extend coaxially with an axis of the tip portion 22 of the catheter 20 (not shown in FIG. 3). The push rod 36 may include a distal portion 38 configured to be attached with a center portion 40 of the electrode 50. In another embodiment, the push rod 36 may be attached to the electrode 50 by way of generally radially-extending struts (not shown) in an umbrella-like configuration. In such a configuration, the struts may be attached symmetrically to various intermediate portions of the electrode 50. In another embodiment, a strut configuration may be used in conjunction with (rather than in place of) attachment of the push rod 36 to the center portion 40 of the electrode 50.

Figure 3A:
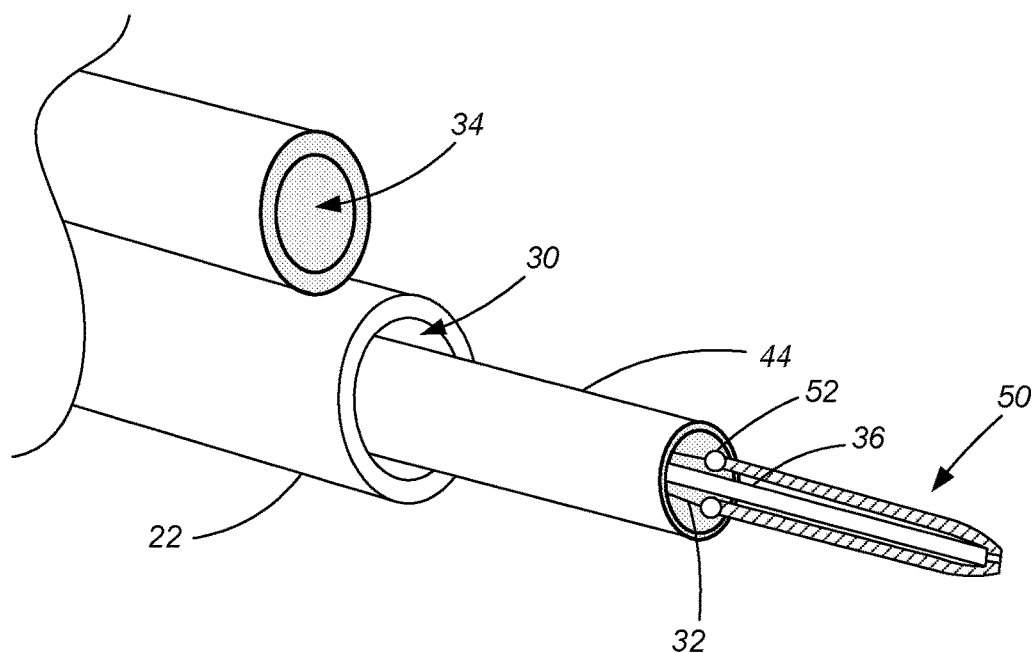
FIG. 3A is a partial cross-sectional view depicting the electrode of FIG. 3 in a constricted configuration being recaptured by the catheter, according to an embodiment of the present invention.

The push rod 36 may be employed to provide a pushing force, indicated by arrow 42, when the electrode 50 is positioned over the ostium of the pulmonary vein. In addition, as depicted in FIGS. 3 and 3A, the push rod 36 can be utilized to act in conjunction with the tethers or lines 32 when recapturing the electrode 50 within the tip portion 22 of the catheter 20. More specifically, the lines 32 may be coupled to the proximal attachment points 52 of the electrode 50 and extend proximally through, for example, an inner sheath 44 or ring. In this manner, the push rod 36 can be used as leverage to hold the distal portion of the electrode 50 steady while the lines 32 are moved proximally (or the inner sheath 44 is moved distally—or both), thereby, pulling the proximal attachment points 52 or ends of the electrode 50 in a radially constricted and narrow configuration to be recaptured within the tip portion 22 of the catheter 20.

Figure 4:
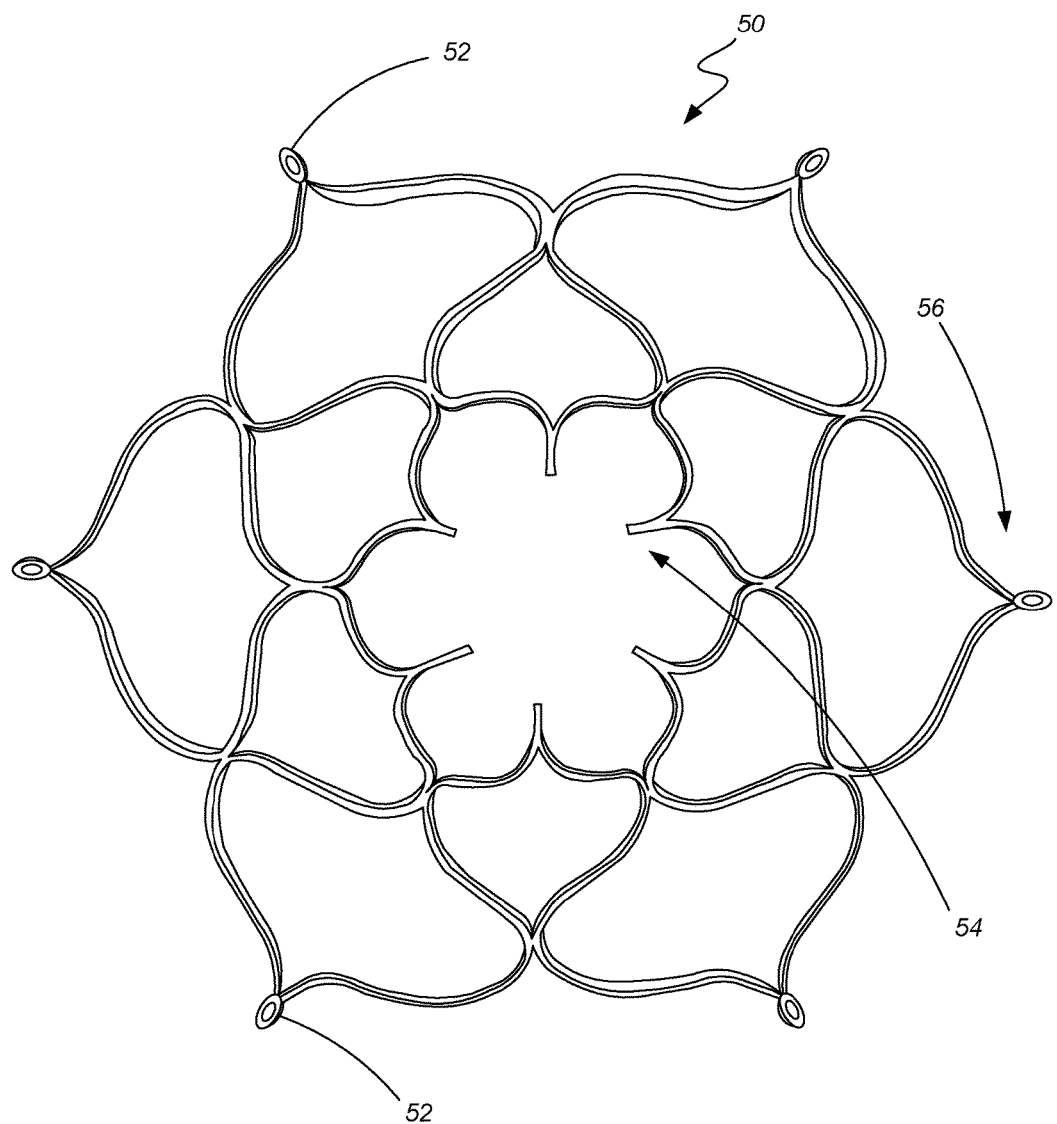
FIGS. 4 and 5 illustrate top and perspective views of the self expanding electrode, according to an embodiment of the present invention.
Figure 5:
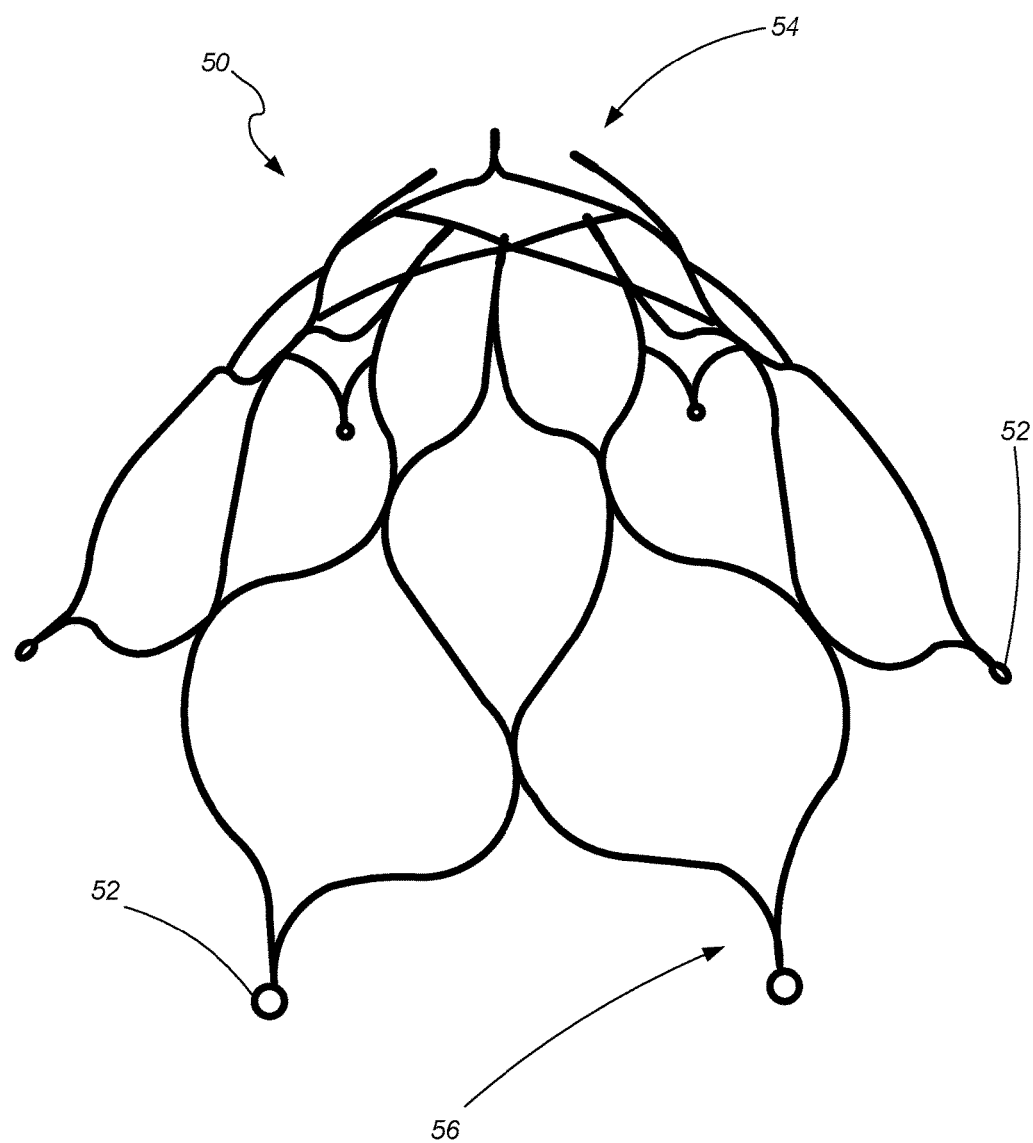

Referring now to FIGS. 4 and 5, the electrode 50 is shown and described in further detail according to one embodiment of the invention. The electrode 50, exhibiting a generally conical or tapered configuration, may include a distal portion 54, which may also be referred to as a tip portion (and may correspond to the center portion 40), and a proximal portion 56 being at an opposite end of the electrode 50. The proximal portion 56 is radially expanded as compared to the distal portion 54. The radially expanded proximal portion 56 may include the attachment points 52 in the form of, for example, eyelets, for attachment of the lines (see, e.g., FIGS. 2 and 3).

In one embodiment, the electrode 50 may be formed from a flat sheet of super elastic material, such as Nitinol material. For example, the electrode 50 can be laser cut from such flat sheet of material and then shaped or heat set to the desired configuration. Such heat setting can be employed in, for example, a heated sand bath utilizing techniques known to those of ordinary skill in the art. It should be noted that the electrode may include, or be formed from, other materials as known in the art.

Figure 6:
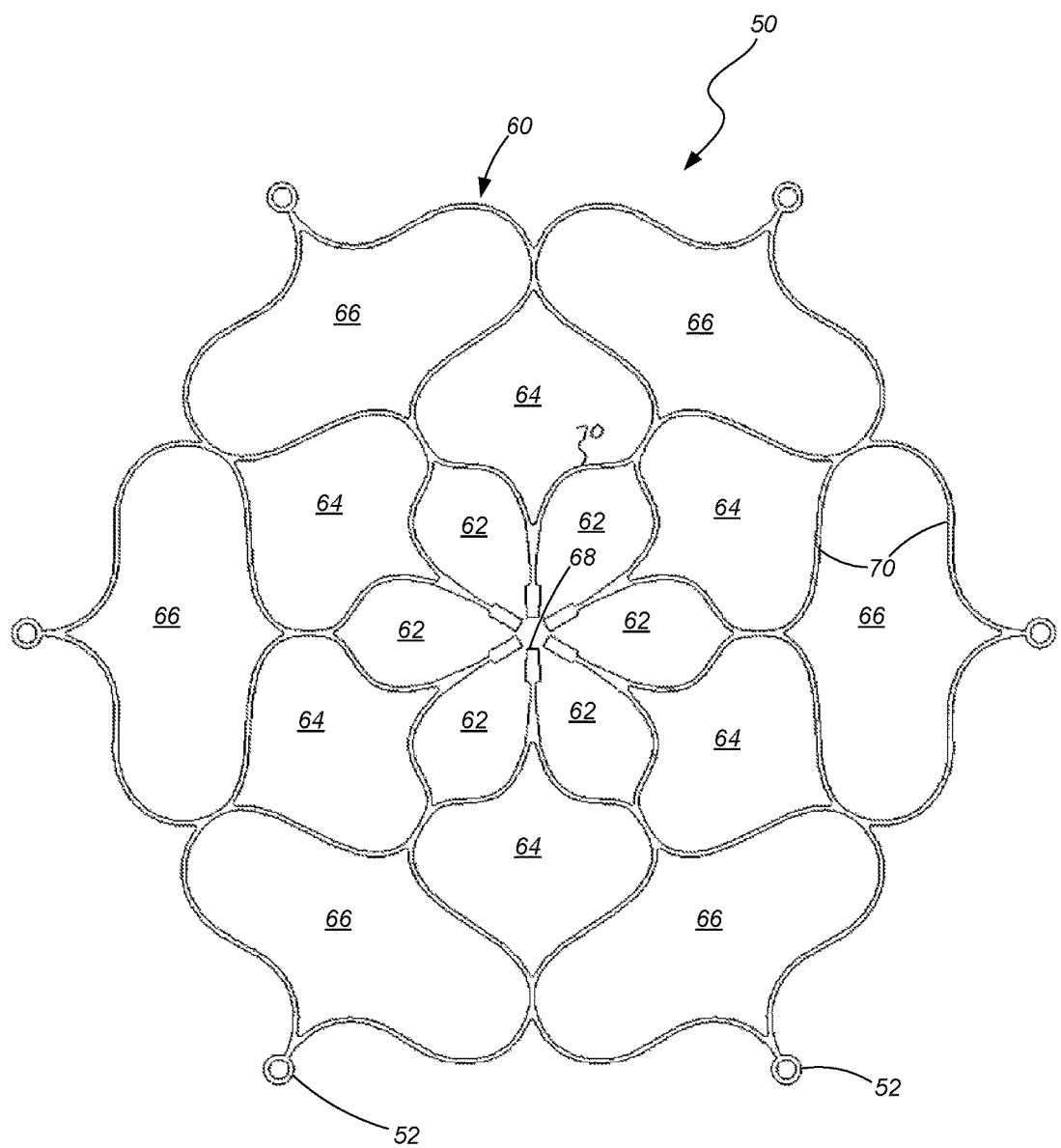
FIGS. 6 and 7 illustrate top and perspective views of the self expanding electrode in a substantially flat configuration, according to another embodiment of the present invention.
Figure 7:
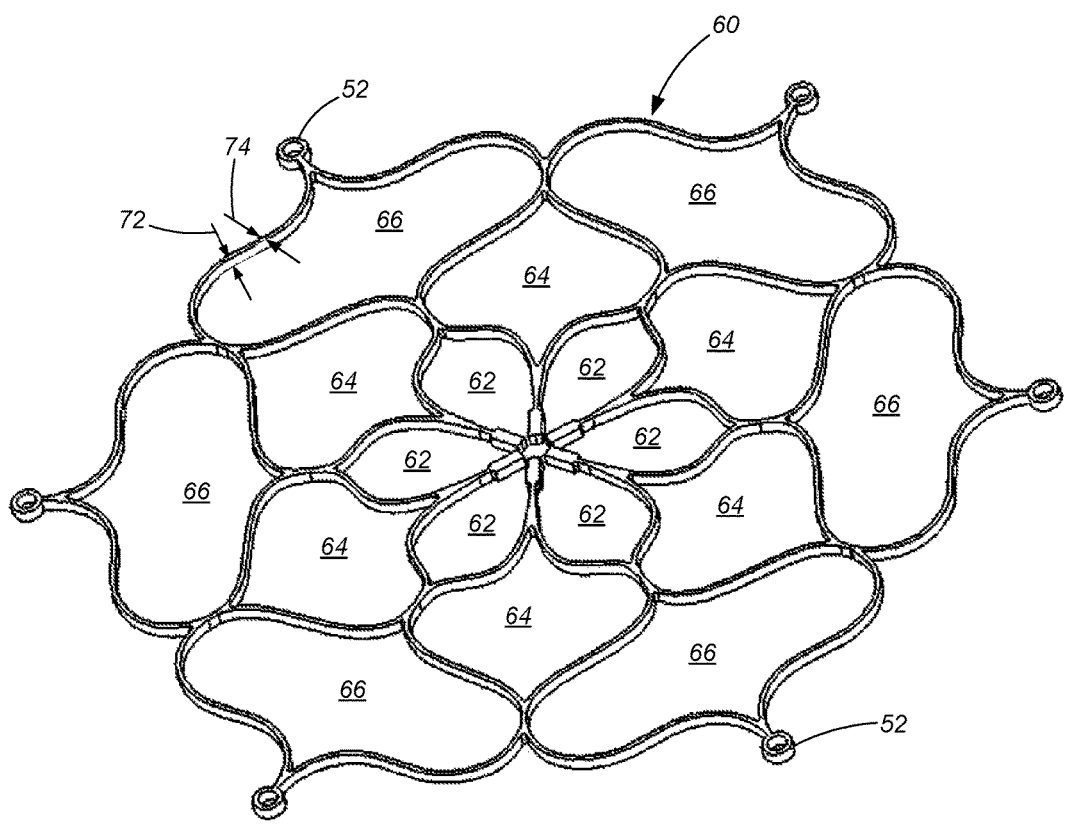

FIGS. 6 and 7 illustrate the electrode 50 during manufacturing thereof prior to shaping or heat setting the electrode such that it exhibits a generally conical configuration. As previously noted, the electrode may be formed from a flat sheet of Nitinol or other appropriate material. In one example, a laser cutting process and an electro polishing process may be used to cut and form the initial configuration of the electrode. Of course, other processes known to those of ordinary skill in the art may similarly be used. The electrode may be formed as a unitary structure. In one embodiment, the electrode 50 can be formed, via a heat setting process, to provide a self expanding conical configuration. In other words, the electrode may be deformed to a constrained configuration (e.g., when stored within the catheter tip prior to deployment) and expand into a desired shape (e.g., generally conical where the proximal end 56 extends radially further than does the distal end 54) upon release from a constricting force (again, such as when released from the catheter tip). In another embodiment, the electrode 50 may self expand from a constricted or collapsed configuration to a substantially flat shape (i.e., the radially outer portion and the center portion lie substantially within the same plane) and be utilized to ablate tissue surrounding the ostium of the pulmonary vein.

It is further noted that, in one embodiment, the electrode 50 may be selectively configured, in terms of shape, size and orientation, during use thereof. For example, the electrode 50, may be used in a flat configuration to treat an area surrounding the ostium of a pulmonary vein, it may be used in a conical configuration to treat a portion of the pulmonary vein or the ostium itself, or it may be selectively configured to exhibit a desired amount of taper between a "flat" configuration and a fully deployed conical configuration. Selectively configuring the geometry of the electrode further enables tailoring of its placement so that ablation of specific tissue may be accomplished more effectively. Such selective configuring may be accomplished, for example, by manipulating the push rod 36 and lines 32 to effect a desired configuration.

As shown in FIGS. 6 and 7, an electrode 50 may include a frame 60 having multiple cells or a multi-cellular configuration. The multi-cellular configuration can include center portion cells 62, intermediate cells 64 and outer cells 66 each being defined by multiple struts 70, the combination of struts 70 and cells (62, 64 and 66) defining the frame 60 or at least a portion thereof. In one embodiment, the center portion cells 62 may collectively exhibit a flower like configuration. The center portion cells 62 may include free ends 68 that each extend toward a center 76 or axis of the frame 60. In such an embodiment, such center portion cells may be considered to be "open" cells since the free ends 68 are not joined to form a closed periphery. during use of the electrode 50, one or more of the free ends 68 may be coupled to the push rod (FIGS. 3 and 3A) for deployment and recapture purposes as discussed above. In another embodiment, the ends of the center portion cells may be interconnected (i.e., not free ends) to form a center cell and, therefore, defining closed periphery cells as the center portion cells 62. In such a case, a push rod may be coupled to a portion of the periphery defining the center cell.

Still referring to FIGS. 6 and 7, the intermediate cells 64 may share common struts 70 adjacent center portion cells 62. In other words, a single strut 70 may be partially define a center portion cell 62 as well as partially define an intermediate cell 64. Similarly, the intermediate cells 64 may share common struts 70 to both the center portion cells 62 and the outer cells 66. In this manner, the center portion cells 62, intermediate cells 64 and the outer cells 66 build upon each other in a radially outward and symmetrical arrangement. It is noted, however, that asymmetrical configurations are also contemplated. Attachment points 52, which may include, for example, an eyelet, may be formed or coupled to a portion (e.g., a radially-most outward portion) of the outer cells 66 for coupling the distal ends of the lines or tethers (see e.g., FIGS. 2 and 3). The frame 60 may also include markers (not shown), such as radio-opaque markers or other markers known in the art, for imaging purposes.

In addition, the struts 70 defining the center portion cells 62 may be symmetrical to one another Likewise, the struts for the intermediate cells 64 may be symmetrical with each other and the struts 70 for the outer cells 66 may be symmetrical with one another. With such an arrangement, the electrode 50 can symmetrically expand and constrict, thereby limiting the strain and stress placed on the struts 70 when moving between an expanded and constricted configuration. Furthermore, the frame 60 can be sized and configured such that the struts 70 for each of the cells can include tapered portions so as to manipulate the behavior of the frame 60, while maintaining structural integrity, when the frame or electrode is moved between the deployed configuration and the constrained configuration within the tip portion of the catheter 20. In other words, a strut may change in cross-sectional area (taken substantially transverse to its length) as it extends along its length. Further, the aspect ratio of a depth 72 and a width 74 of the struts can be manipulated to increase the structural integrity of the frame 60 when being moved between expanded and constricted configurations.

Figure 8A:
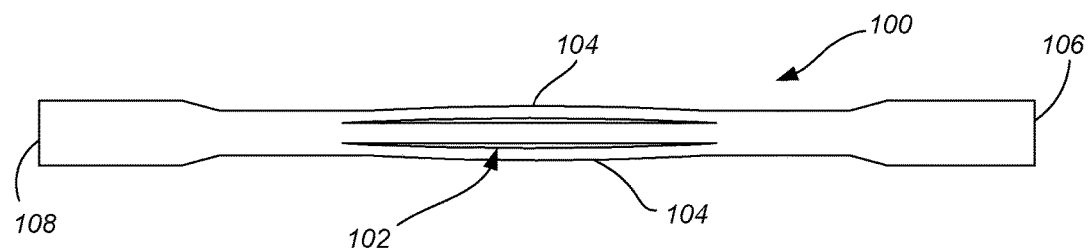
FIGS. 8A-8C illustrate an electrode according to an embodiment of the present invention.
Figure 8B:
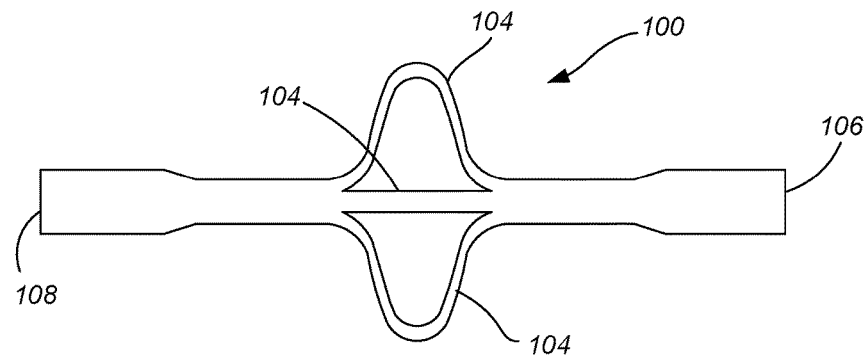
Figure 8C:
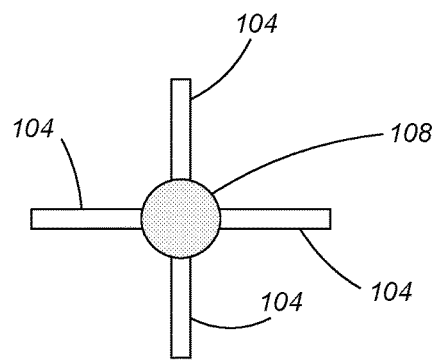

Referring now to FIGS. 8A-8C, an electrode 100 is shown in accordance with another embodiment of the present invention. The electrode 100 may be formed from a tube having cuts or slits 102 formed along a portion of its length. The cuts or slits 102 define strut members 104. The electrode 100 may take the form as shown in FIG. 8A when disposed within a catheter (not shown) for delivery to a desired location within a patient's heart. When in the delivery configuration, the struts 104 are substantially elongated. When deployed, the longitudinal ends 106 and 108 of the electrode 104 may be displaced toward one another (such as by push rods, tethers and the like) such that the struts 104 become curved or bent and have portions displaced radially outward as indicated in FIGS. 8B and 8C. The radially outward portions of the struts 104 may then be used to contact a desired area within the heart, such as the pulmonary vein, the ostium of the pulmonary vein or surrounding tissue. When the ablation procedure is complete, the electrode 100 may be recaptured within a catheter by displacing the ends 106 and 108 away from each other so that the struts 104 are again elongated (such as shown in FIG. 8A) and electrode may be drawn back into the catheter. It is noted that a similarly shaped electrode may be formed by other means such as by use of wire or other material wherein the electrode is self expanding to the configuration shown in FIGS. 8B and 8C. While four struts are shown to be used in FIGS. 8A-8C, such is not to be considered limiting and other numbers of struts are contemplated as being utilized.

Figure 9:
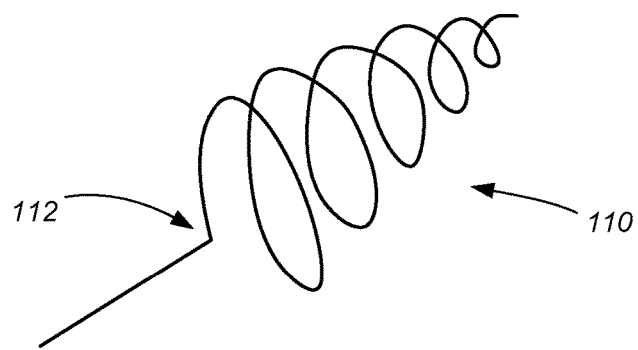
FIGS. 9 and 10 illustrate electrodes according to additional embodiments of the present invention.
Figure 10:
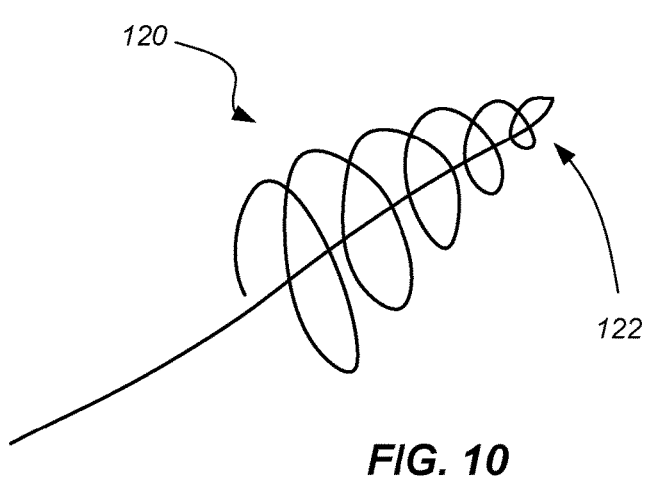

Referring briefly to FIG. 9, another electrode 110 is shown which exhibits a configuration of a substantially helical coil. A similarly shaped electrode 120 is shown in FIG. 10. The electrode 110 of FIG. 9 is configured to be a connected at a proximal end 112 thereof, while the electrode 120 of FIG. 10 is configured with a connection at a distal end 122 thereof. Such electrodes 110 and 120 may be formed of wire, a shape memory alloy, or from other appropriate material.

Figure 11:
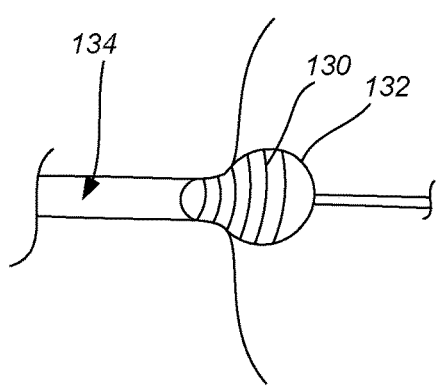
FIG. 11 shows an electrode with an expansion device according to an embodiment of the present invention.

Referring briefly to FIG. 11, an electrode 130 is shown having an expansion device 132 associated therewith. The expansion device 132 may include, for example, a balloon or self-expanding foam. The use of an expansion device 132 may assist in expanding the electrode and effecting contact of the electrode with the surrounding tissue. Additionally, the expansion device 132 may be used to help center or otherwise position the electrode with respect to the pulmonary vein 134.

Figure 12:
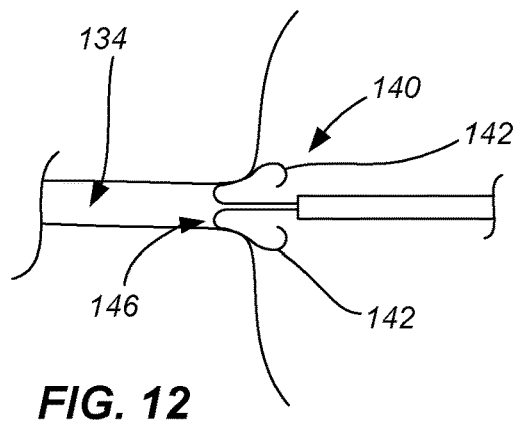
FIG. 12 shows an electrode according to yet another embodiment of the present invention.

FIG. 12 shows another embodiment of an electrode 140 that includes multiple arms 142 shaped and configured to engage the ostium of a pulmonary vein 134. The arms 142 may include distal portions 146 sized and shaped to enter the pulmonary vein 134, while the arms 142 flare radially outwardly so as to have a portion of the electrode 140 that is wider than ostium and, therefore contacts or engages the ostium (and/or tissue surrounding the ostium) of the pulmonary vein 134.

Figure 13:
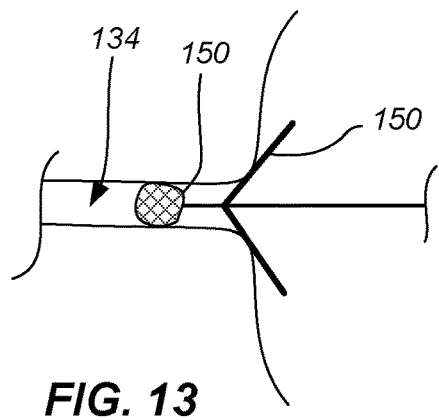
FIGS. 13 and 14 show electrodes utilized with centering devices according to an embodiment of the present invention.
Figure 14:
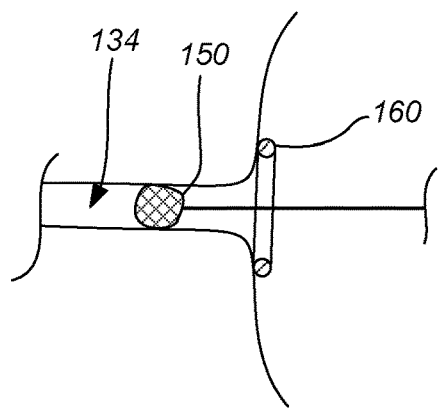
Figure 15A:
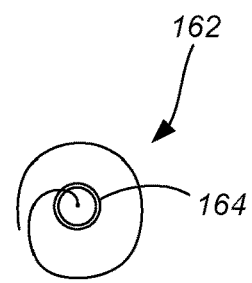
FIGS. 15A and 15B illustrate electrodes according to additional embodiments of the present invention.
Figure 15B:
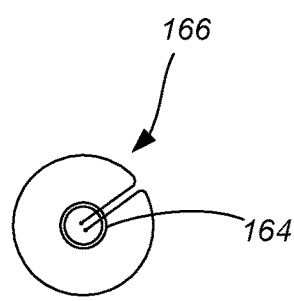

Referring briefly to FIG. 13, an electrode 150 is shown that is associated with a centering device 152. The centering device 152 may include, for example, expandable foam, a balloon, or some other body or resilient material. The centering device 152 may be disposed within the pulmonary vein 134 so as to assist in positioning the electrode 150 at a desired location. The electrode may be configured according to any of the various electrodes described herein or even according to known electrode configurations. For example, FIG. 14 shows a similar mechanism having a centering device 152 with a differently configured electrode 160. The electrode shown in FIG. 14 includes a generally ring shaped structure which may be configured as an open loop 162 with a single end of the electrode 160 extending through the catheter 164, as shown in FIG. 15A, or as a closed loop 166 with two ends of the electrode extending into the catheter 164, as shown in FIG. 15B.

Figure 16A:
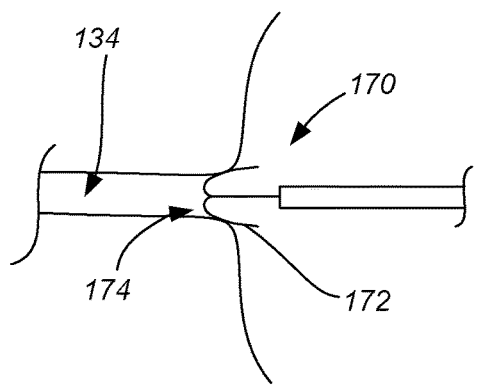
FIGS. 16A and 16B illustrate electrodes according to additional embodiments of the present invention.
Figure 16B:
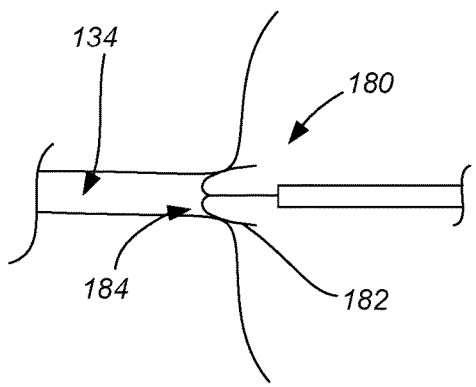

Referring briefly to FIGS. 16A and 16B, further embodiments of electrodes 170 and 180 are shown. The electrodes 170 and 180 generally have multiple aims 172 and 182 shaped and configured to engage the ostium of a pulmonary vein 134. The arms 172 and 182 may include distal portions 174 and 184 sized and shaped to enter the pulmonary vein 134, while the arms 172 and 182 flare radially outwardly so as to have a portion of the electrodes 170 and 180 that is wider than ostium and, therefore contacts or engages the ostium of the pulmonary vein 134. The electrode 180 shown in FIG. 16B is formed in a closed loop configuration as compared the electrode 170 shown in FIG. 16A.

Figure 17A:
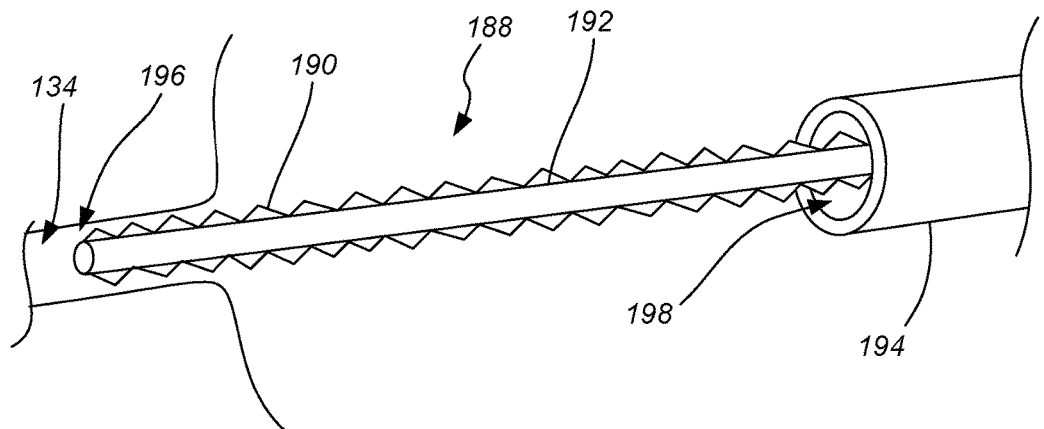
FIGS. 17A and 17B show an electrode and catheter system according to an embodiment of the present invention.
Figure 17B:
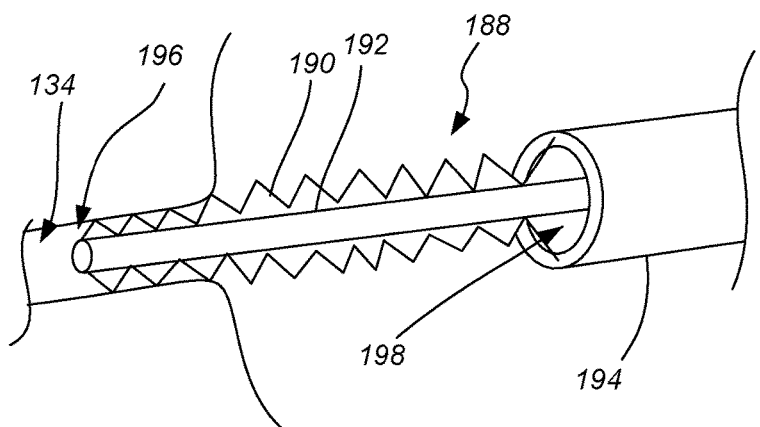

Referring now to FIGS. 17A and 17B, an electrode 188 in accordance with another embodiment of the present invention is shown. The electrode 188 includes a radially expanding structure 190 such as a stent-like device or a resilient polymer structure. The radially expanding structure 190 may extend along a push-rod 192 or other structure and be radially constricted such that it fits within a lumen of a catheter 194. A distal end 196 of the radially expanding structure may be coupled with the push-rod 192 while a proximal end 198 of the push-rod 192 may be configured, when released from the lumen of the catheter 194, to abut against a surface of the catheter 194. The catheter 194 and push rod 192 may then be displaced relative to each other, such as shown in FIG. 17B, so that the radially expanding structure 190 becomes shortened and expands radially. The electrode 188, having been expanded radially, now contacts tissue within the pulmonary vein 134, at the ostium, or both. The push-rod 192 may act as a centering device to help locate the electrode 188 relative to the pulmonary vein 134. Tethers, or other mechanisms (not shown), may be coupled with the proximal end of the radially expanding structure 190 to help recapture the electrode for repositioning or after an ablation process is complete.

Figure 18:
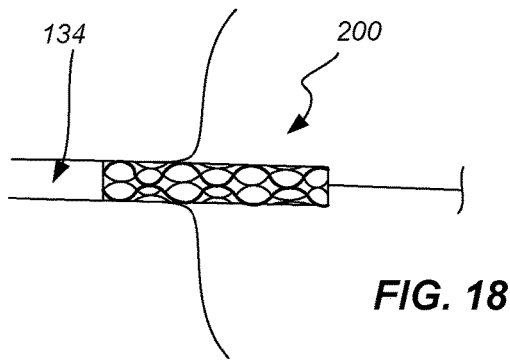
FIG. 18 shows an electrode according to another embodiment of the present invention.

Referring to FIG. 18, another electrode 200 may include a more conventional stent-like device that is expanded, for example, by a balloon or other mechanism to engage tissue associated with a pulmonary vein 134.

Figure 19A:
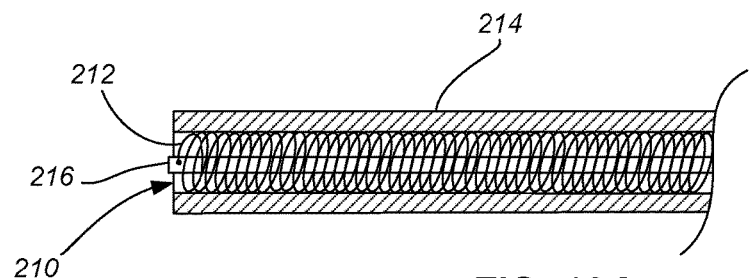
Figure 19B:
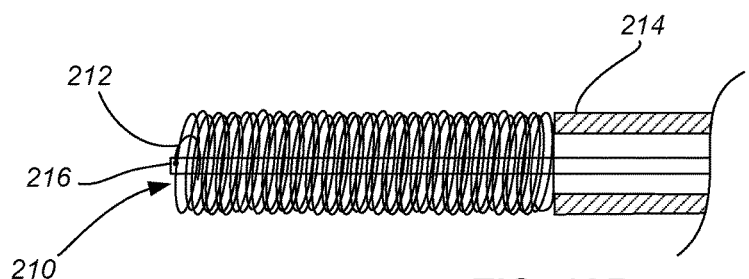
Figure 19C:
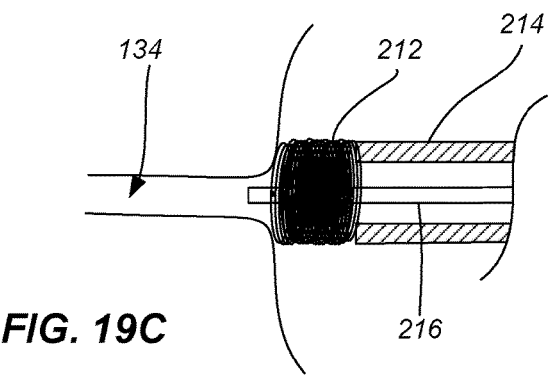

Referring to FIGS. 19A-19C, an electrode 210 according to another embodiment may include a spring 212 or other helical spring-like structure contained within a lumen of a catheter 214. A push-rod 216 may be coupled to a distal end of the spring 212 to assist in deploying the spring 212 from the catheter 214. While in the catheter 214, the spring 212 may be radially constricted such that it expands radially when released from the lumen as indicated in FIG. 19B. A proximal end of the spring 212 may then abut a surface of the catheter (e.g., an end surface) and the catheter 214 and push-rod 216 may be displaced relative to each other to shorten the length of the spring 212. The longitudinally compressed spring 212 may then be placed in contact with the ostium of the pulmonary vein 134 as indicated in FIG. 19C. The electrode may be recaptured in a manner such as previously described. It is noted that the electrode may also be deployed and recaptured by twisting the ends of the spring 212 relative to each other so as to alter the diameter of the spring 212.

Referring briefly to FIG. 20 a annular electrode 220 is shown as an example of a bipolar electrode having a conductive inner surface 222 which may act as a first pole and a conductive outer surface 224 may act as a another pole. The two conductive surfaces 222 and 224 may be separated from one another by a dielectric material 226. In such a configuration, separate leads from an RF generator, for example, may be coupled with the conductive surfaces 222 and 224 causing current to flow from one ring or surface (e.g., 222) to another (e.g. 224).

In another embodiment, as shown in FIG. 21, an annular electrode 230 may be segmented longitudinally so as to have alternating poles around the circumference of the electrode. The segments 232 are electrically isolated from one another such that current flows from one segment, through tissue contacting or adjacent the segment, and to another segment of an opposite polarity.

In accordance with another embodiment, as shown in FIG. 22, a capacitively coupled electrode is shown wherein a segmented catheter 240 is placed adjacent tissue to be ablated. A selectively positioned electrode 242 is positioned within the catheter 240 providing a selectively adjustable ablation point. The ablation point is determined by the relative location of between electrode 242 and the segmented catheter 240. Thus, the ablation point may be adjusted by repositioning the electrode 242 within the catheter 240. Such an embodiment might be configured to utilize either a unipolar or bipolar electrode.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. An ablation system, comprising:
a delivery device having a sheath extending to a distal end, the delivery device including a push rod and multiple tethers;
an ablation energy source operatively coupled to the delivery device; and
an ablation member coupled to the push rod and the multiple tethers, the ablation member extending with multiple struts to define a multi-cellular structure, the ablation member configured to be coupled to the ablation energy source and configured to be disposed adjacent the distal end of the sheath, the ablation member configured to receive ablation energy for treating tissue, the ablation member being coupled to the push rod and the multiple tethers to facilitate moving the ablation member from an expanded configuration to a narrow configuration for capturing the ablation member within the sheath.

2. The ablation system of claim 1, wherein the ablation member is configured to self-expand upon being deployed from the distal end of the delivery device.

3. The ablation system of claim 1, wherein the expanded configuration of the ablation member exhibits a substantially conical configuration.

4. The ablation system of claim 1, wherein the ablation member is configured to radially expand to the expanded configuration.

5. The ablation system of claim 1, wherein one or more of the multiple struts include tapered portions along a length thereof.

6. The ablation system of claim 1, wherein the ablation member comprises one or more sensors configured to sense characteristics of the tissue.

7. The ablation system of claim 6, further comprising a controller coupled to the ablation energy source, the controller configured to receive signals measured by the one or more sensors.

8. The ablation system of claim 1, wherein the ablation member comprises a super elastic material.

9. The ablation system of claim 1, wherein the ablation member is an electrode frame.

10. The ablation system of claim 1, wherein the ablation energy source is an RF energy source.

11. An ablation system, comprising:
a delivery device having a handle with a sheath extending from the handle, the delivery device having a push rod and tethers coupled to the handle; and
an ablation member coupled to the push rod and the tethers, the ablation member configured to be constrained within the delivery device adjacent a distal end of the sheath and configured to be deployed from the distal end of the sheath to be movable to an expanded configuration, the ablation member extending with multiple struts to exhibit a conical configuration.

12. The ablation system of claim 11, wherein the ablation member is configured to self-expand upon being deployed from the distal end of the sheath.

13. The ablation system of claim 11, wherein one or more of the multiple struts include tapered portions along a length thereof.

14. The ablation system of claim 11, wherein the ablation member comprises one or more sensors configured to sense characteristics of the tissue.

15. The ablation system of claim 11, further comprising an ablation energy source operatively coupled to the ablation member and configured to provide ablation energy to the ablation member to treat tissue.

16. The ablation system of claim 15, further comprising a controller coupled to the ablation energy source.

17. The ablation system of claim 16, wherein the ablation member comprises one or more sensors configured to sense characteristics of the tissue such that the controller is configured to receive signals measured by the one or more sensors.

18. The ablation system of claim 15, wherein the ablation energy source comprises an RF energy source.

19. The ablation system of claim 11, wherein the ablation member comprises a super elastic material.

20. The ablation system of claim 11, wherein the ablation member comprises an electrode.

* * * * *